(12) United States Patent
Kiraly

(10) Patent No.: US 8,301,224 B2
(45) Date of Patent: Oct. 30, 2012

(54) SYSTEM AND METHOD FOR AUTOMATIC, NON-INVASIVE DIAGNOSIS OF PULMONARY HYPERTENSION AND MEASUREMENT OF MEAN PULMONARY ARTERIAL PRESSURE

(75) Inventor: Atilla Peter Kiraly, Plainsboro, NJ (US)

(73) Assignee: Siemens Aktiengesellschaft, München (DE)

( * ) Notice: Subject to any disclaimer, the term of this patent is extended or adjusted under 35 U.S.C. 154(b) by 511 days.

(21) Appl. No.: 12/557,689

(22) Filed: Sep. 11, 2009

(65) Prior Publication Data
US 2010/0094122 A1   Apr. 15, 2010

Related U.S. Application Data

(60) Provisional application No. 61/104,086, filed on Oct. 9, 2008.

(51) Int. Cl.
A61B 5/00 (2006.01)
A61B 5/055 (2006.01)

(52) U.S. Cl. ........ 600/410; 600/310; 600/411; 600/413; 600/419; 600/481; 382/128

(58) Field of Classification Search .......... 600/301, 600/410, 411, 413, 419, 481; 382/128
See application file for complete search history.

(56) References Cited

U.S. PATENT DOCUMENTS 5,830,143 A * 11/1998 Mistretta et al. ............. 600/420
7,194,117 B2 * 3/2007 Kaufman et al. ............. 382/128

OTHER PUBLICATIONS

Reiter et al. Magnetic Resonance-Derived 3-Dimensional Blood Flow Patterns in the Main Pulmonary Artery as a Marker of Pulmonary Hypertension and a Measure of Elevated Mean Pulmonary Arterial Pressure. Circ Cardiovasc Imaging. Jul. 2008;1(1):23-30.*
Kozerke et al. Automatic Vessel Segmentation Using Active Contours in Cine Phase Contrast Flow Measurements. J Magn Reson Imaging 10: 41-51, 1999.*
Heiberg et al. Three-Dimensional Flow Characterization Using Vector Pattern Matching. IEEE Transactions on Visualization and Computer Graphics, vol. 9 No. 3 Jul.-Sep. 2003.*
Sadarjoen et al. Selective Visualization of Vortices in Hydrodynamic Flows. Proc. IEEE Visualization 1998, pp. 419-422, 1998.*
Jiang et al. Detection and Visualization of Vortices. The Visualization Handbook pp. 295-309, Academic Press 2005.*

* cited by examiner

*Primary Examiner* — Brian Casler
*Assistant Examiner* — Phong K Huynh
(74) *Attorney, Agent, or Firm* — Donald B. Paschburg; F. Chau & Associates, LLC

(57) ABSTRACT

A method for diagnosing pulmonary hypertension from phase-contrast magnetic resonance (MR) images includes providing a time series of one or more magnetic resonance (MR) flow images of a patient's mediastinum during one or more cardiac cycles, segmenting the pulmonary artery within each image of the times series of images, identifying the anterior wall and pulmonary valve within the segmented pulmonary artery, analyzing blood flow during a diastolic phase of the one or more cardiac cycles to determine a relative duration of blood flow, $t_{streamlines}$, during the diastolic phase, analyzing blood flow during a latter portion of a systolic phase and a subsequent diastolic phase of the one or more cardiac cycles to detect the presence and duration $t_{vortex}$ of a vortex, and diagnosing the presence of pulmonary hypertension from $t_{streamlines}$ and $t_{vortex}$.

32 Claims, 9 Drawing Sheets

SYSTEM AND METHOD FOR AUTOMATIC, NON-INVASIVE DIAGNOSIS OF PULMONARY HYPERTENSION AND MEASUREMENT OF MEAN PULMONARY ARTERIAL PRESSURE

CROSS REFERENCE TO RELATED UNITED STATES APPLICATIONS

This application claims priority from "Automatic, non-invasive approach to Diagnosis of Pulmonary Hypertension and Measurement of Mean Pulmonary Arterial Pressure", U.S. Provisional Application No. 61/104,086 of Atilla Kiraly, filed Oct. 9, 2008, the contents of which are herein incorporated by reference in their entirety.

TECHNICAL FIELD

This disclosure is directed to computer-assisted methods for diagnosing pulmonary hypertension and measuring mean pulmonary arterial pressure from phase contrast magnetic resonance (MR) images.

DISCUSSION OF THE RELATED ART

Pulmonary hypertension (PH) is the condition of elevated pressure in the pulmonary artery. Current clinical methods of diagnosing and accessing severity of PH involve an invasive procedure of right heart catherization. However, a recent study, G. Reiter, U. Reiter, G. Kovacs, B. Kainz, K. Schmidt, R. Maier, H. Olshewski, and R. Reinmueller, "Magnetic Resonance-Derived 3-Dimensional Blood Flow Patterns in the Main Pulmonary Artery as a Marker of Pulmonary Hypertension and a Measure of Elevated Mean Pulmonary Arterial Pressure", Circ. Cardiovascular Imaging, 2008, the contents of which are herein incorporated by reference in their entirety, has demonstrated the ability to detect and distinguish between types of PH through non-invasive field-contrast MRI. Depending upon flow patterns, researchers have been able to distinguish from normal cases, latent PH, and manifest PH (most severe).

This study investigated 3 features of the flow field in the main pulmonary artery. The first feature was the existence of vortices in the primary flow direction in the main pulmonary artery. In general, a vortex is defined as a ring- or spiral-shaped motion of fluid or gas. In terms of the vector field representation of blood flow, this means the formation of concentric ring- or spiral-shaped curves in the main pulmonary artery to which velocity vectors are tangential. A vortex in the primary flow direction in the main pulmonary artery means that there is forward and backward flow through a cross section of the main pulmonary artery through the center of the vortex. The existence of such a vortex may be characterized by $t_{vortex}$, the relative period of existence of a nonvalvular vortex in the main pulmonary artery, determined by dividing the number of cardiac phases with a vortex by the total number of imaged cardiac phases. FIG. 1(A) depicts a vortex in a pulmonary artery PA. The arrows in the diagram indicate blood flow across a cross section, indicated by the dashes line. The pulmonary valve PV, the right ventricle RV, the anterior wall a, and the posterior wall p are indicated in the figure, with forward flow along the anterior wall a and backward flow along the posterior wall p.

The second specific feature was the diastolic streamline of blood flow upward along the anterior wall of the main pulmonary artery. In terms of the vector field representation of blood flow, this means that blood moves continuously up the anterior wall of the main pulmonary artery during diastole. The diastolic stream may be characterized by $t_{streamlines}$, the relative duration of existence of diastolic streamlines, calculated by dividing the number of cardiac phases after pulmonary valve closure with streamlines along the main pulmonary artery by the total number of imaged cardiac phases. FIG. 1(B) depicts flow streamlines along the PA anterior wall used to calculate $t_{streamlines}$, with the same reference labels as FIG. 1(A).

Third, a location index was introduced to characterize the velocity profile of blood flow above the pulmonary valve in the anterior-posterior direction. Depending on whether the maximum velocity through the cross section of the main pulmonary artery appeared in the anterior, middle, or posterior third of the vessel, the location index was set to +1, 0, or −1, respectively. The maximum velocities in the section thirds were interpreted as being different if their difference exceeded a typical pixel-by-pixel variation of velocities. In the case of equal maximum velocities in multiple sections, the location index was set to the average value of the corresponding thirds. The location index was determined in the cardiac phase with maximum pulmonary outflow, as well as in the cardiac phase of pulmonary valve closure. FIG. 1(C) depicts blood flow vectors in each of the three regions of the PA above the pulmonary valve: the anterior region a, the middle region m, and the posterior region p. For each region, a maximum vector is indicated by, respectively, $v_{max,\ a}$, $v_{max,\ m}$, and $v_{max,\ p}$.

At maximum outflow, flow profiles were distributed homogenously across the cross sections of the main pulmonary artery in the manifest PH group, the latent PH group, and the normal group. In the later systole phase, a vortex was formed in the manifest PH group. No such vortex could be found in the latent PH group or the normal group. After pulmonary valve closure, the vortex in the PH group persisted for some time. In all cases, a continuous diastolic blood flow upward along the anterior wall of the main pulmonary artery could be observed. Although this phenomenon disappeared quickly in controls, it was observed significantly longer in latent PH and manifest PH. Thus, the time $t_{streamlines}$ allowed for good distinction between all three classes of patients. In addition, for patients with manifest PH, the mean Pulmo-Arterial Pressure (mPAP) was capable of being estimated directly from $t_{vortex}$. The results were shown to be statistically significant. Although further studies are necessary, the initial results are very promising.

These results were based on manually measuring and identifying these features within the pulmonary artery (PA). However, this image-based procedure is manually intensive and may not be suited for clinical usage due to the tedious effort necessary to obtain these features. A computer assisted method of automatically computing such features would allow for clinical utility.

The images used in the above experiments are seven-dimensional (7D) images of the chest obtained through magnetic resonance imaging (MRI) that can capture blood velocity and magnitude through vessels. Each 3D voxel within the image contains anatomical information in the form of a gray level value and a 3D vector indicating the direction and magnitude of movement. All data values are recorded over the time of one or more heart cycles. These additional data can prove invaluable for the segmentation of vasculature in such images.

7D MRI scans comprise a series of volumes quickly acquired over time, so that each 7D MRI image corresponds to a time point. For each 3D location within a volume, there is a gray-level related to anatomical information as well as a vector. Hence, the vector field is part of the data given from the scanner and no additional effort of any kind is required to obtain the vector field.

Quantifying blood flow is important in diagnosing a number of different heart conditions, such as pulmonary hypertension. Using MRI for this purpose has a number of advantages, as it is non-invasive and does not affect the flow that is being measured. Furthermore, with MRI it is possible to obtain flow measurements in any direction, and can simultaneously measure velocity of blood flow and lumen area, which aids in making accurate flow estimations.

The ability to measure flow with MRI was developed in the 1980's for in vivo use. There are two groups of techniques for flow measurements with MRI: phase techniques, and time-of-flight techniques. Imaging techniques that utilize phase changes are more widely used and include phase contrast (PC) imaging and the less frequently used Fourier velocity imaging.

The quantitative measurement of flow velocity by MR imaging is based on acquiring two types of images: (1) a flow sensitized image, i.e. an image of which the contents are affected by the velocity of moving matter, typically flowing blood; and (2) an image whose contents are not affected by the motion, known as a flow compensated image. The image acquisition process is based on a particular sequence of magnetic gradient and RF pulses. The phase difference of these complex valued images is linearly related to the velocity, and may be set by a user. In cardiac phase contrast flow studies, there are three types of MR images: (1) a phase image, which is a phase reconstruction of the difference signal; (2) an anatomy (rephased) image, which is a magnitude reconstruction of the flow-compensated signal; and (3) a magnitude image, which is a magnitude reconstruction of the difference signal.

The basis of magnetic resonance imaging is that when nuclei possessing a half-integer spin are placed inside a magnetic field, their magnetic moments will precess around the axis of the field. The frequency with which they will precess is called their resonance or Larmor frequency. Altering the intensity of the magnetic field will change the rate at which spins precess. The gradients used in MRI are fields with linearly varying intensity that are added to the main magnetic field. Applying a gradient to the field will thus alter the resonance frequency of spins. This means that since nuclei at different positions will experience different fields, they will also precess at different frequencies. The change in frequency will lead to an accumulation of phase, which is dependent on the frequency shift and the time it is applied. It is this phase shift that is utilized in phase contrast MRI to yield information about the motion of nuclei. Since the change in phase is directly dependent on the alteration in frequency, it is dependant on how far spins travel, which is an effect of their velocity.

Phase contrast MRI is based on the property that a uniform motion of tissue in a magnetic field gradient produces a change in the MR signal phase, $\Phi$. This change is proportional to the velocity of the tissue, v. The MR signal from a volume element accumulates the phase $$\Phi(r,t)=\gamma B_0 T+\gamma v \cdot \int G(r,t)t dt = \gamma B_0 T + \gamma v \cdot \overline{G},$$

during time T, where $B_0$ is a static magnetic field, $\gamma$ the gyro-magnetic ratio and $G(r, t)$ is the magnetic field gradient. Notice that $\overline{G}$ is exactly the first moment of $G(r, t)$ with respect to time. If the field gradient is altered between two consecutive recordings, then by subtracting the resulting phases $$\Phi_1-\Phi_2=\gamma v \cdot (\overline{G}_1-\overline{G}_2)$$

the velocity in the $(\overline{G}_1-\overline{G}_2)$-direction is implicitly given. In this way a desired velocity component can be calculated for every volume element simultaneously. To construct the velocity vector in 3D, the natural way is to apply appropriate gradients to produce the x-, y- and z-components respectively. The velocity can be expressed in vector form $v=(v_x, v_y, v_z)^T$, and the velocity magnitude is $|v|=\sqrt{v \cdot v}=\sqrt{v_x^2+v_y^2+v_z^2}$.

SUMMARY OF THE INVENTION

Exemplary embodiments of the invention as described herein generally include methods and systems for a fully automatic analysis of a field-contrast MRI images to automatically segment the PA and quantify flow parameters for automatic diagnosis and quantification of Pulmonary Hypertension. An analysis of the flow within the PA according to an embodiment of the invention can yield a diagnosis for PH, and, for the case of malignant PH, mPAP values can be estimated. In addition, an approach according to an embodiment of the invention can help automate further studies using field-contrast MRI to evaluate PH. With additional clinical studies, a method according to an embodiment of the invention can replace invasive heart catheterization procedures to diagnose PH. Concurrently, a method according to an embodiment of the invention can be used to increase workflow and allow for more datasets to be analyzed.

According to an aspect of the invention, there is provided a method for diagnosing pulmonary hypertension from phase-contrast magnetic resonance (MR) images, including providing a time series of one or more magnetic resonance (MR) flow images of a patient's mediastinum during one or more cardiac cycles, where each flow image for a given time point comprises a plurality of 3-dimensional flow vectors associated with a 3-dimensional grid of points, segmenting the pulmonary artery within each image of the times series of images, and identifying the anterior wall and pulmonary valve within the segmented pulmonary artery, analyzing blood flow during a diastolic phase of the one or more cardiac cycles to determine a relative duration of blood flow, $t_{streamlines}$, during the diastolic phase, analyzing blood flow during a latter portion of a systolic phase and a subsequent diastolic phase of the one or more cardiac cycles to detect the presence and duration $t_{vortex}$ of a vortex, and diagnosing the presence of pulmonary hypertension from $t_{streamlines}$ and $t_{vortex}$.

According to a further aspect of the invention, the method includes determining the systolic and diastolic phases of each cardiac cycle from electrocardiography data acquired with the time series of the MR flow images.

According to a further aspect of the invention, the method includes determining the systolic and diastolic phases of each cardiac cycle by analyzing blood flow during the one or more cardiac cycles and identifying time points of maximal and minimal blood flow.

According to a further aspect of the invention, the method includes computing a centerline of the pulmonary artery, and using the centerline to locate the pulmonary valve.

According to a further aspect of the invention, analyzing blood flow to determine $t_{streamlines}$ comprises selecting an image from the time series of images that is associated with a beginning of a diastolic phase, calculating in the selected image a spatial average of the flow magnitude in a spatial region in a cross section of the pulmonary artery, calculating the spatial average of the flow magnitude in each subsequent image associated with the diastolic phase until an end image is reached where the spatial average falls below a predetermined threshold, and determining $t_{streamlines}$ from differences in a time associated with the image associated with the beginning of a diastolic phase and a time associated with the end image.

According to a further aspect of the invention, the spatial region in the cross section of the pulmonary artery is adjacent to the anterior wall of the pulmonary artery.

According to a further aspect of the invention, analyzing blood flow to detect a vortex comprises selecting an image from the time series of images that is associated with a systolic phase of a cardiac cycle, selecting a candidate vortex center point in the selected image, forming a first vector from the candidate vortex center point to a second point, the second point having a radius with respect to the first point, forming a second vector from the flow vector associated with the second point, calculating a sine of an angle formed by the first and second vector, for a set of second points forming a circle of the radius, repeating the steps of forming a second vector from a flow vector associated with the second point, and calculating a sine of an angle formed by the first and second vector, where the sines are summed, where the sum of sines is indicative of the presence of a vortex.

According to a further aspect of the invention, the method includes repeating the steps of forming a second vector from a flow vector associated with the second point, and calculating a sine of an angle formed by the first and second vector, where the sines are summed, for sets of points with different radii with respect to the candidate center point.

According to a further aspect of the invention, the method includes the steps of, for a detected vortex, measuring in subsequent images a sine of an angle between a first vector from a corresponding candidate vortex center point to a second point having the radius with respect to the candidate vortex center point and a second vector formed from the flow vector associated with the second point until an end image where the sum of sines falls below a predetermined threshold, and determining a time $t_{vortex}$ by subtracting a time associated with the image associated with the detection of the vortex from a time associated with the end image.

According to a further aspect of the invention, analyzing blood flow to detect a vortex comprises selecting a set of seed points uniformly spaced in a cross section of the pulmonary artery above the pulmonary valve, computing a streamline for each seed point by repeating steps of advancing each seed point to a new point in a direction of the flow vector associated with each seed point, and resetting each seed point to each corresponding new point, for a predetermined number of iterations, and searching the streamlines for a circular pattern, where a circular pattern indicates the presence of a vortex.

According to a further aspect of the invention, the method includes the steps of, for a detected vortex, calculating in subsequent images a corresponding streamline for a seed point whose streamline may be part of a vortex, until an end image is reached where the corresponding streamline and its neighboring streamlines no longer forms part of a vortex, and determining a time $t_{vortex}$ from differences in a time associated with the image associated with the detection of the vortex and a time associated with the end image.

According to a further aspect of the invention, the method includes dividing a cross section of the pulmonary artery above and near to the pulmonary valve into an anterior region, a middle region, and a posterior region, calculating a maximal flow velocity magnitude in each region for each image in at least one cardiac phase in the time series of images, selecting a location in an image in each cardiac phase having a greatest maximal flow velocity magnitude, and assigning a location index a value indicative of in which of the anterior region, the middle region, and the posterior region the greatest maximal flow velocity magnitude occurred, where the location index characterizes a blood flow velocity profile.

According to a further aspect of the invention, if two or more regions have substantially a same greatest maximal flow velocity magnitude, assigning the location index to the average value of the corresponding regions.

According to another aspect of the invention, there is provided a method for diagnosing pulmonary hypertension from phase-contrast magnetic resonance (MR) images, including the steps of providing a time series of one or more magnetic resonance (MR) flow images of a patient's mediastinum during one or more cardiac cycles, where each flow image for a given time point comprises a plurality of 3-dimensional flow vectors associated with a 3-dimensional grid of points, segmenting the pulmonary artery within each image of the times series of images, and identifying the anterior wall and pulmonary valve within the segmented pulmonary artery, dividing a cross section of the pulmonary artery above and near to the pulmonary valve into an anterior region, a middle region, and a posterior region, calculating a maximal flow velocity magnitude in each region for each image in the time series of images, selecting a location having a greatest maximal flow velocity magnitude over the time series of images, assigning a location index a value indicative of in which of the anterior region, the middle region, and the posterior region the greatest maximal flow velocity magnitude occurred, where the location index characterizes a blood flow velocity profile, and diagnosing the presence of pulmonary hypertension by analyzing the location index in at least one cardiac phase in the time series of images.

According to a further aspect of the invention, the method includes selecting a location in an image in each phase of a cardiac cycle having a greatest maximal flow velocity magnitude; and determining a location index for each phase by assigning a value indicative of in which of the anterior region, the middle region, and the posterior region the greatest maximal flow velocity magnitude occurred.

According to a further aspect of the invention, the method includes selecting a location in each image in the time series of images having a greatest maximal flow velocity magnitude; and determining a location index for each phase by assigning a value indicative of in which of the anterior region, the middle region, and the posterior region the greatest maximal flow velocity magnitude occurred.

According to a further aspect of the invention, if two or more regions have substantially a same greatest maximal flow velocity magnitude, assigning the location index to the average value of the corresponding regions.

According to a further aspect of the invention, the method includes analyzing to blood flow during a diastolic phase of the one or more cardiac cycles to determine a relative duration of blood flow, $t_{streamlines}$, during the diastolic phase, and analyzing blood flow during a latter portion of a systolic phase and a subsequent diastolic phase of the one or more cardiac cycles to detect the presence and duration $t_{vortex}$ of a vortex.

According to a further aspect of the invention, the method includes using a distance transform to divide the pulmonary artery cross section into the three regions.

According to another aspect of the invention, there is provided a program storage device readable by a computer, tangibly embodying a program of instructions executable by the computer to perform the method steps for diagnosing pulmonary hypertension from phase-contrast magnetic resonance (MR) images.

DETAILED DESCRIPTION OF EXEMPLARY EMBODIMENTS

Figure 1:
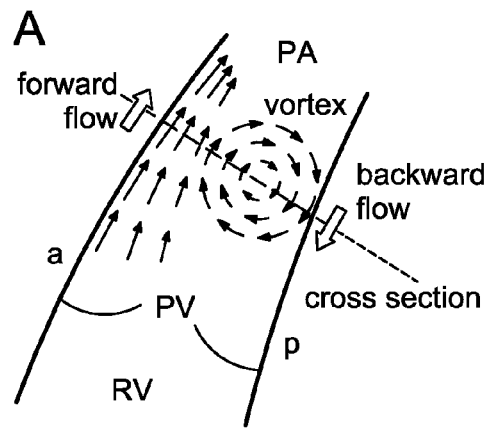
FIGS. 1(A)-(C) illustrate the specific flow features measured in the main pulmonary artery, according to an embodiment of the invention.
Figure 1:
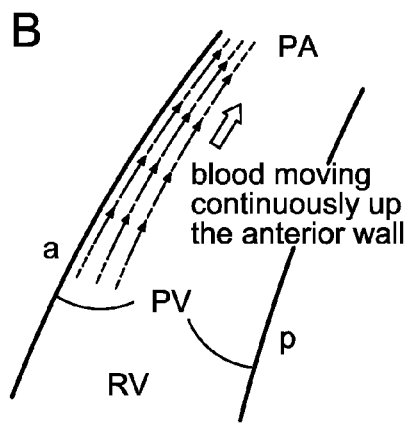
Figure 1:
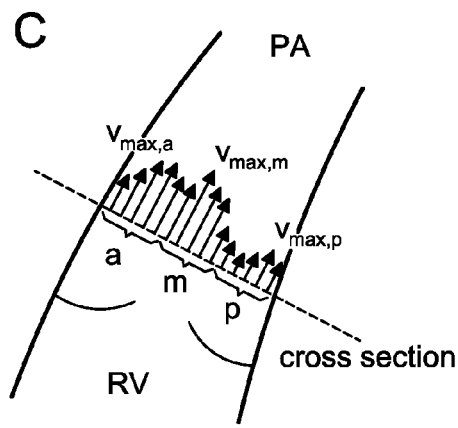

Exemplary embodiments of the invention as described herein generally include systems and methods for automatic, non-invasive diagnosis of pulmonary hypertension and estimation of mean pulmonary arterial pressure from phase contrast magnetic resonance (MR) images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 2:
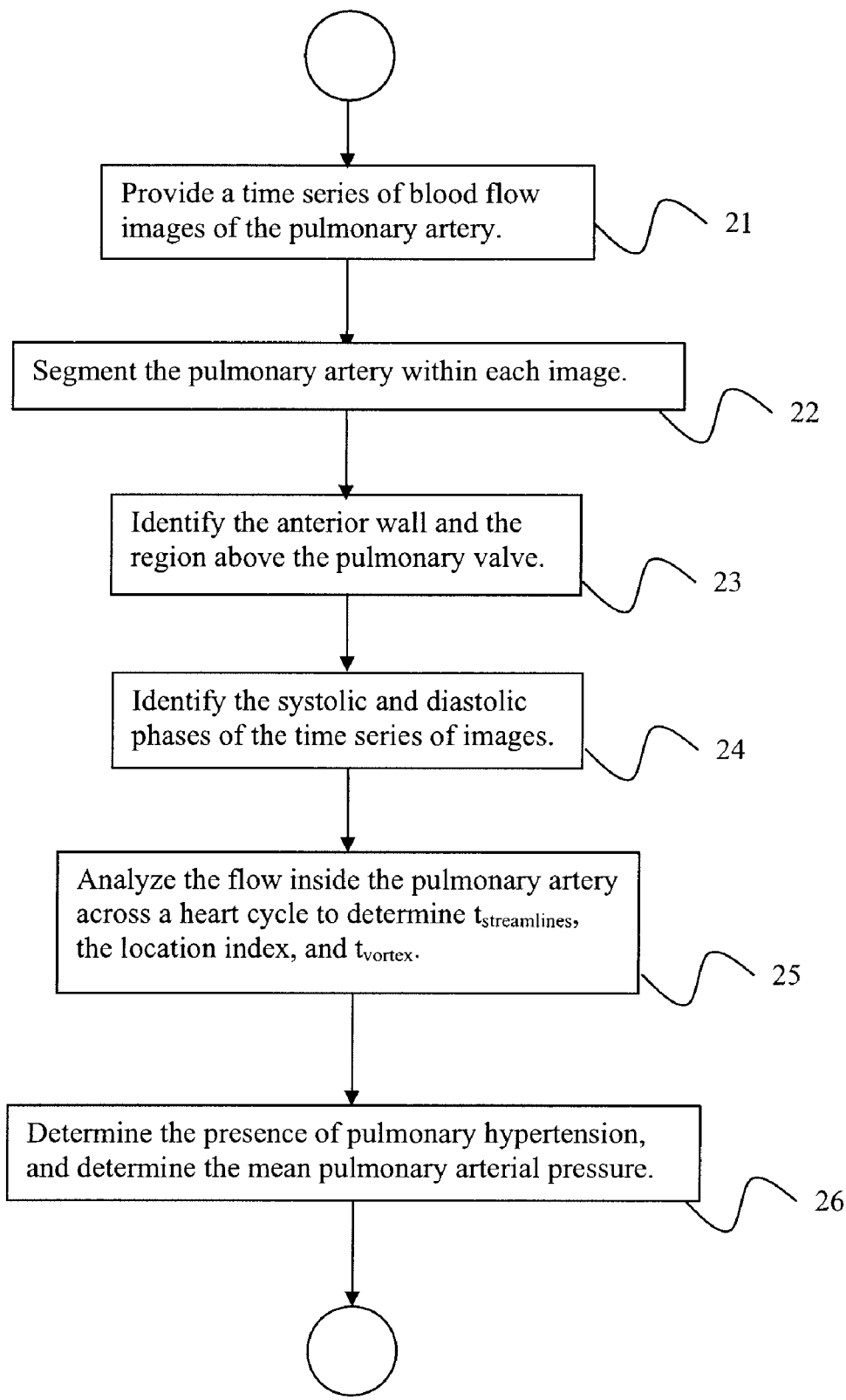
FIG. 2 is a flowchart of a method for automatic, non-invasive diagnosis of pulmonary hypertension and measurement of mean pulmonary arterial pressure from phase contrast magnetic resonance (MR) images, according to an embodiment of the invention.

A flowchart of a method according to an embodiment of the invention is presented in FIG. 2. An automatic non-invasive method according to an embodiment of the invention for diagnosing both latent and manifest PH and measuring mPAP in cases of manifest PH begins at step 21 by providing a time series of blood flow images of the PA, such as those obtainable from MR phase-contrast images. The PA is then automatically segmented at step 22 within each 3D time frame to acquire the centerlines and the inner wall. Next, at step 23, two components of the PA are identified: the anterior wall and the region above the pulmonary valve (PV). Before or during the segmentation process, at step 24, the systole and diastolic phases of the time sequence need to be determined. The systolic phase is when the flow is maximal and the heart is pumping, while the diastolic phase is when the heart is at rest with minimal flow. This information can be obtained from EKG data if available, or by analyzing the flow velocities in the PA to determine the points of maximal and minimal flow. For example, the flow in the aortic arch and the PA can be analyzed to determine the correct cardiac phase of the time series. The flow inside the PA across the heart cycle is then analyzed at step 25 within the PA to determine $t_{streamlines}$, the length of time of any diastolic streamlines in the anterior wall and of the PA, the location index, as well as $t_{vortex}$, the detection and timing of any vortices. Image processing methods involving segmentation and filtering are used to achieve these measurements. These values are used at step 26 to diagnose PH and in the case of malignant PH, determine a value for mPAP.

Figure 3:
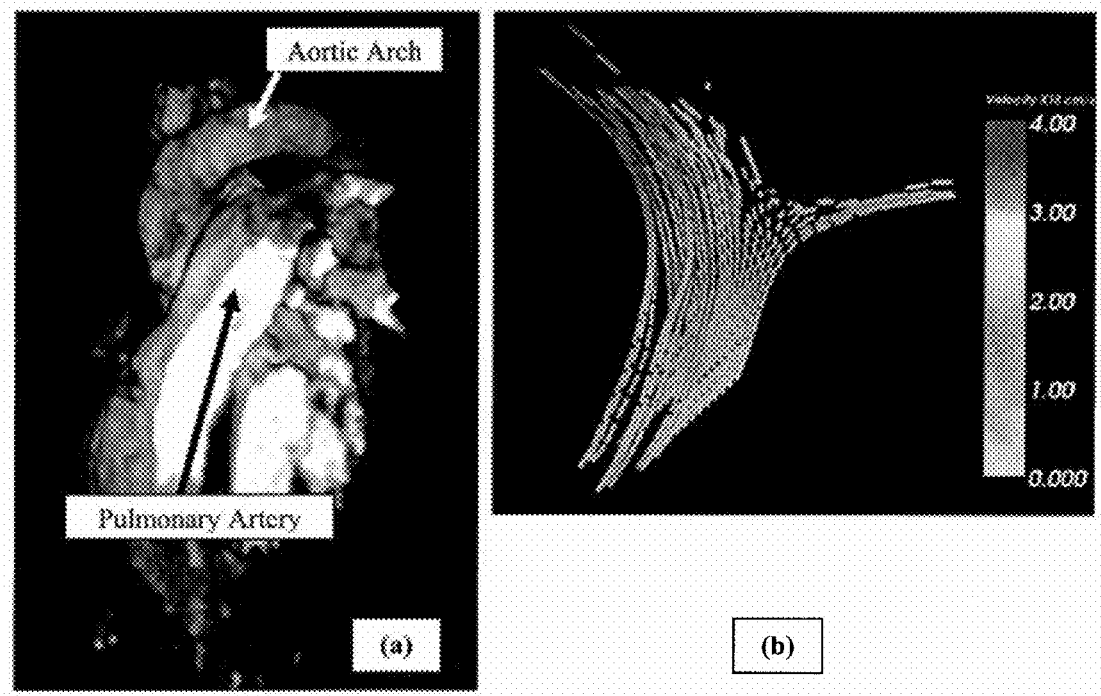
FIG. 3(a) shows a volume rendering of an exemplary anatomical image of the chest.
FIG. 3(b) depicts a particle-based stream line of the flow within the PA, according to an embodiment of the invention.

FIG. 3(a) shows a volume rendering of an exemplary anatomical image of the chest. The pulmonary artery (PA) and aortic arch are labeled. FIG. 3(b) depicts a particle-based stream line of the flow within the PA as computed from the flow data during one complete heart cycle. Quantification of the flow within the PA is possible with this data. The flow shown in FIG. 3(b) is indicative of a patient without any signs of PH.

The PA may be segmented using both the anatomical image and flow image, or just using the anatomical image by itself. There are many methods known in the art for segmenting the PA. A list of exemplary, non-limiting methods includes methods proposed in this inventor's co-pending application, U.S. Patent Publication No. 2008/0044072 of Kiraly, et al., entitled "Method For Automatic Separation of Segmented Tubular and Circular Objects", filed on Jun. 14, 2007, the contents of which are herein incorporated by reference in their entirety, an atlas based approach in which a labeled atlas is first registered to the input image after which the registered labels are then used for probability distributions for tissue labeling method based on local probabilities, and methods based on Markov Random Fields (MRF).

The segmentation results include segmented and labeled structures within the mediastinum. The PA segmentation can then be analyzed relative to the patient coordinates to determine the anterior wall and the location of the pulmonary valve. This process is straightforward in that the once the patient orientation is known, the anterior (back of the patient) and other corresponding regions of the PA are known as well. The anterior of the PA is then simply the wall of the PA that is facing the back of the patient, and the PV is the beginning of the PA According to another embodiment of the invention, one may compute the centerline of the PA to better understand its geometry. For example, knowing the bifurcation location of the PA allows one to better determine the pulmonary value location.

Given knowledge of the cardiac phase, the region near the anterior PA can be analyzed. $t_{streamlines}$ can be calculated as the time duration of significant flow across the region near the anterior PA occurring during the diastolic phase.

Figure 4:
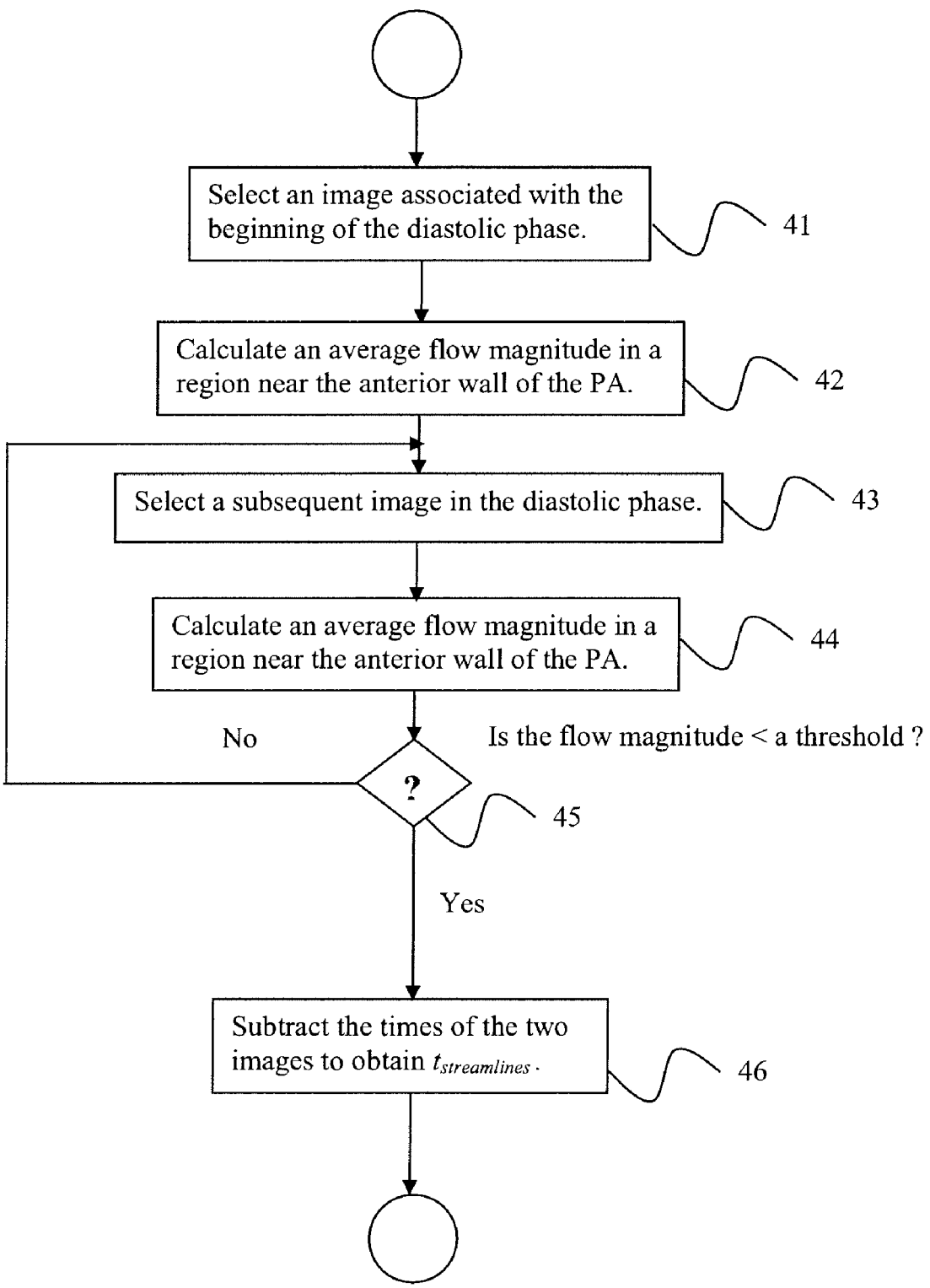
FIG. 4 is a flowchart of a method for computing $t_{streamlines}$, according to an embodiment of the invention.

FIG. 4 is a flowchart of a method for computing $t_{streamlines}$, according to an embodiment of the invention. One begins the computation of $t_{streamlines}$ at step 41 by selecting an image associated with the beginning of the diastolic phase, and calculating, at step 42, an average flow magnitude in a region near the anterior wall of the PA. This region is determined from the segmentation of the PA. A subsequent image in the diastolic phase is selected at step 44, and its average flow magnitude is calculated in the same region near the anterior wall at step 45. Steps 44 and 45 are repeated until, at step 46, the spatially averaged flow magnitude drops below a threshold. At step 47, one subtracts the times of the two images to obtain the $t_{streamlines}$ time.

Figure 5:
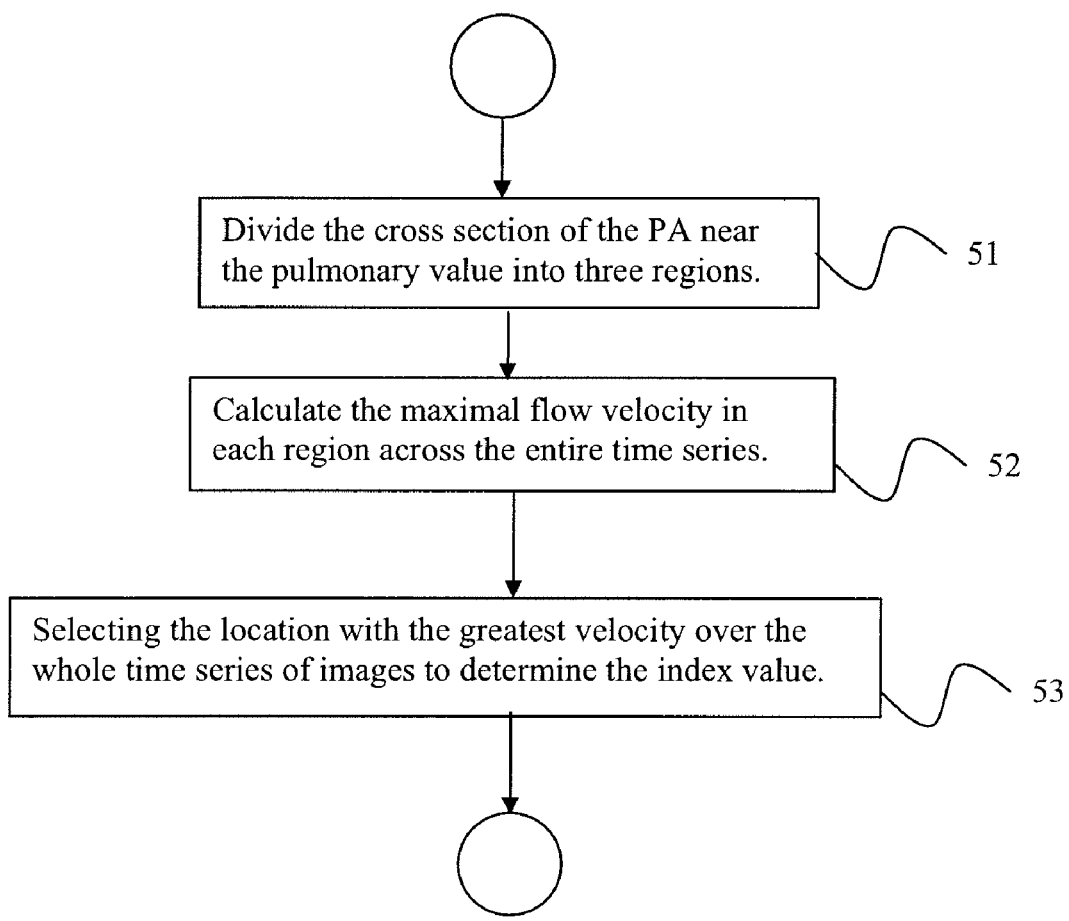
FIG. 5 is a flowchart of a method for computing the location index, according to an embodiment of the invention.

FIG. 5 is a flowchart of a method for computing the location index, according to an embodiment of the invention. To determine the location index, the cross section of the PA is first divided at step 51, into three regions near the pulmonary value: an anterior third, a middle third, and a posterior third of the vessel. As stated above, depending on whether the maximum velocity appears in the anterior, middle, or posterior third of the vessel, the location index is set to +1, 0, or −1, respectively. A 2D distance transform across a projection of the PA allows for an appropriate division of the regions. Given the 2D distance transform from one side, the PA can be separated into the three regions based upon the distance values. At step 52, the maximal flow velocity in each region across the entire time series is calculated and recorded. For this purpose, a magnitude image can be computed on the fly as needed from the velocity vectors in the flow images of the time series There are several possibilities for determining the location index (or indices). According to one embodiment of the invention, the location with the greatest velocity over the whole time series is selected at step 53 as the index value. However, the value for the anterior and middle section could come from two different phases. A second maximal value is determined from all three locations to assign the location index. For example, if the middle region achieved the maximal velocity, then the index would be 0. According to another embodiment of the invention, a location index is computed for each cardiac phase in the time series of images. According to another embodiment of the invention, the location index could be computed at each image of the time series, except when there is no blood flowing. In this embodiment, the location indices would likely change during cardiac phases, and could provide useful results when correlated with other data. Similarly, in the case of substantially equal maximum velocities in multiple sections, the location index was set to the average value of the corresponding thirds.

Figure 6A:
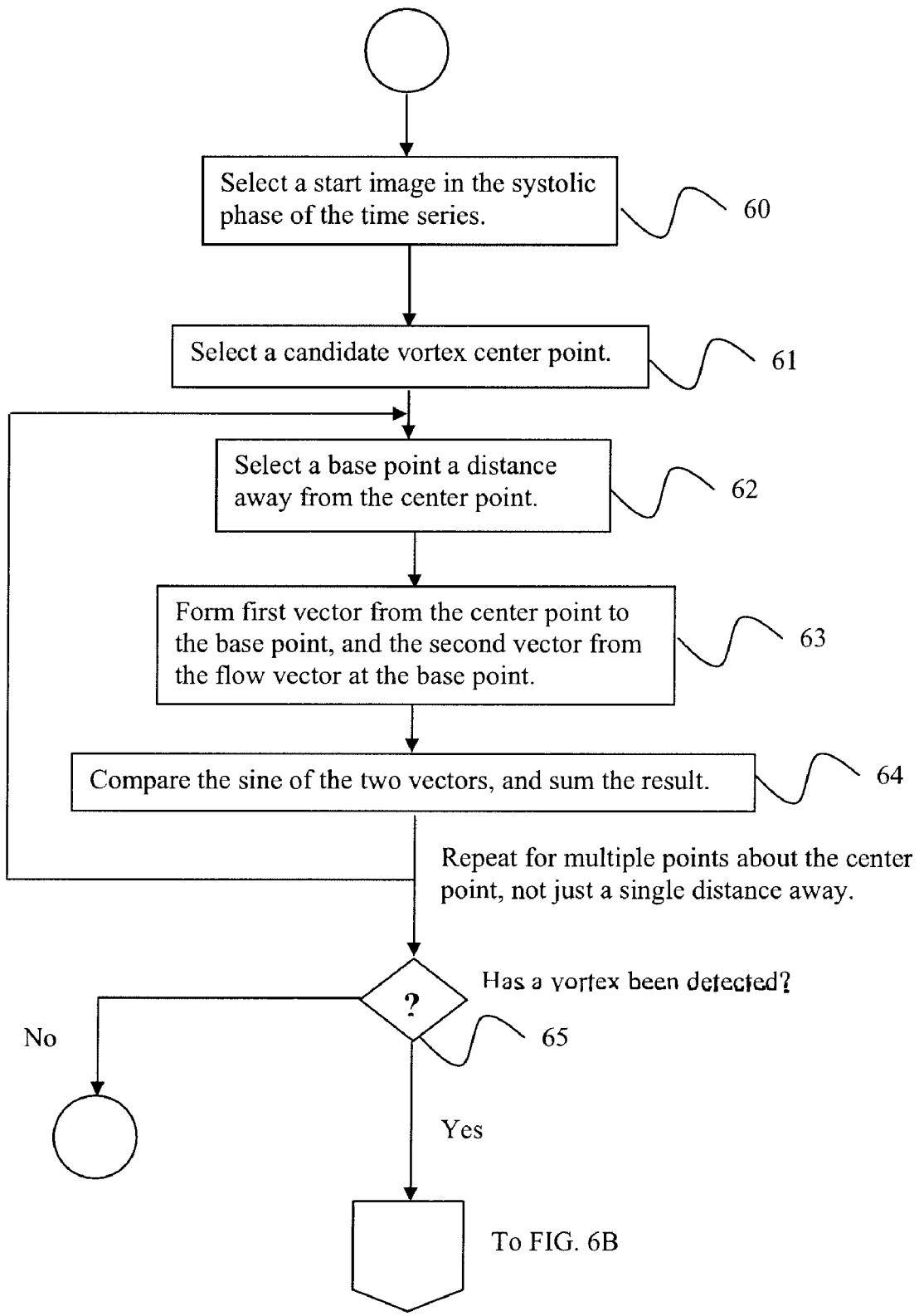
FIGS. 6A-B is a flowchart of a method for detecting a vortex and calculating $t_{vortex}$, according to an embodiment of the invention.
Figure 6B:
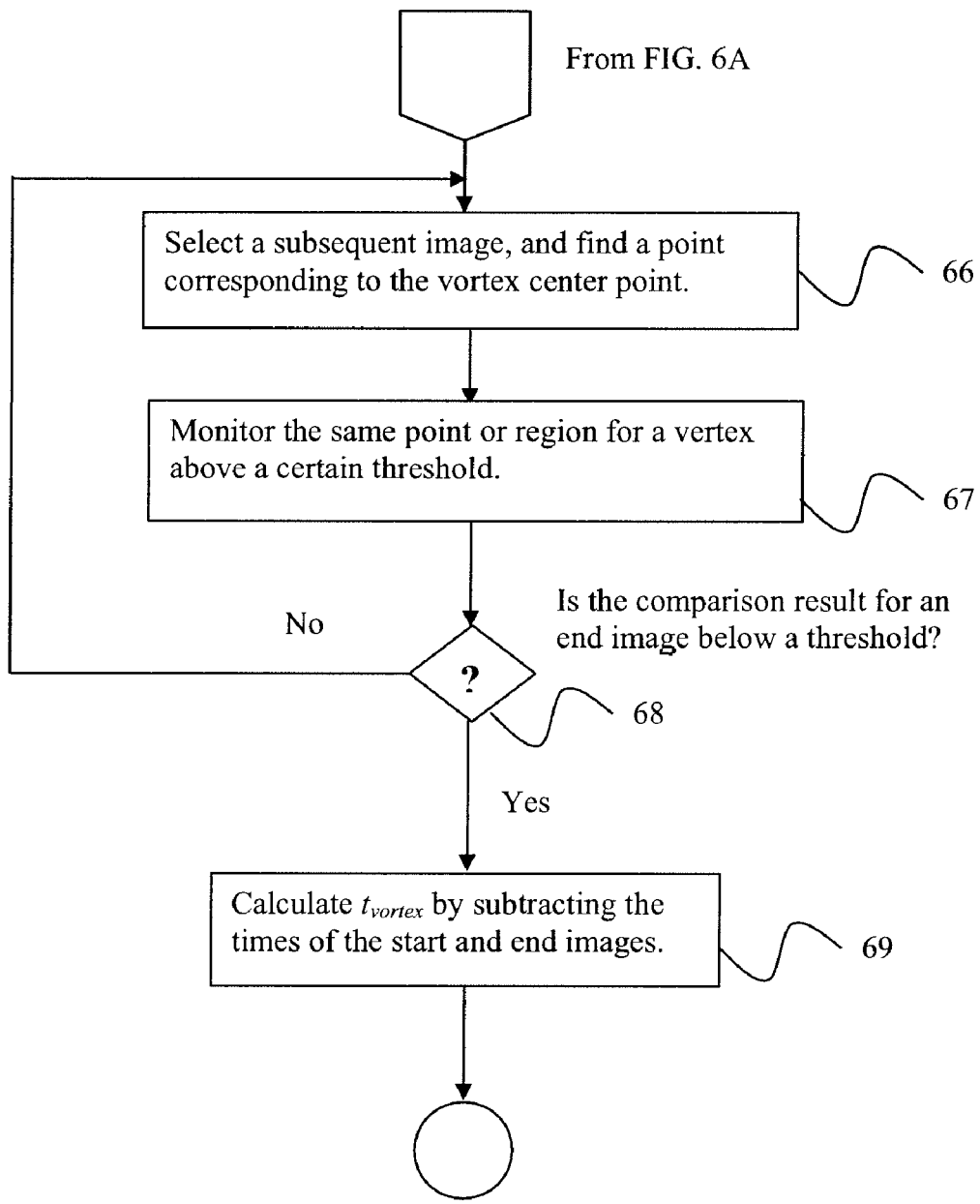

FIGS. 6A-B is a flowchart of a method for detecting a vortex and calculating $t_{vortex}$, according to an embodiment of the invention. A vortex may be detected by performing a series of computations comparing the direction of two vectors in a single, selected image. Referring to FIG. 6A, a method for detecting a vortex begins at step 60 by selecting a start image in the systolic phase of the time series. Note that the start image is actually several images since the images form a 7D dataset. A candidate vortex center point is selected at step 61, and a base point is selected at step 62 that is a distance away from the candidate center point. The following computations are then performed at all points within a certain distance to the candidate center point within the PA. At step 63, the first vector is formed from the candidate vortex center point to the base point, and the second vector is formed the flow vector at the base point. The vectors are compared at step 64, and the comparison result is the sine of the angle formed by these two vectors, which is maximal when they are perpendicular. The magnitude of the flow vector can be used to scale the result. By repeating steps 62, 63, and 64, a series of comparisons in a disk of set radius around the candidate center point are obtained the comparison result is summed. From this accumulated result, one can obtain a numerical value indicating the likelihood of a vortex at a particular location. The result is a measure that is high for vortex region and low for other regions. Once, at step 65, a vortex has been detected, one can determine how long it exists by continually measuring a particular point or region throughout the time series, until an image where the detection measure falls below a threshold. Thus, moving on the FIG. 6B, at step 66, a subsequent image is selected, and a point corresponding to the vortex center point is found. At step 67, a single base point is selected, and the above sums are computed. Steps 66 and 67 are repeated until, at step 68, the comparison result for an end image is below a threshold, after which $t_{vortex}$ is obtained at step 69 by subtracting the times of the start and end images. The computation can be limited to those images of the time series where the ejection is occurring, that is, during the systole.

Figure 7:
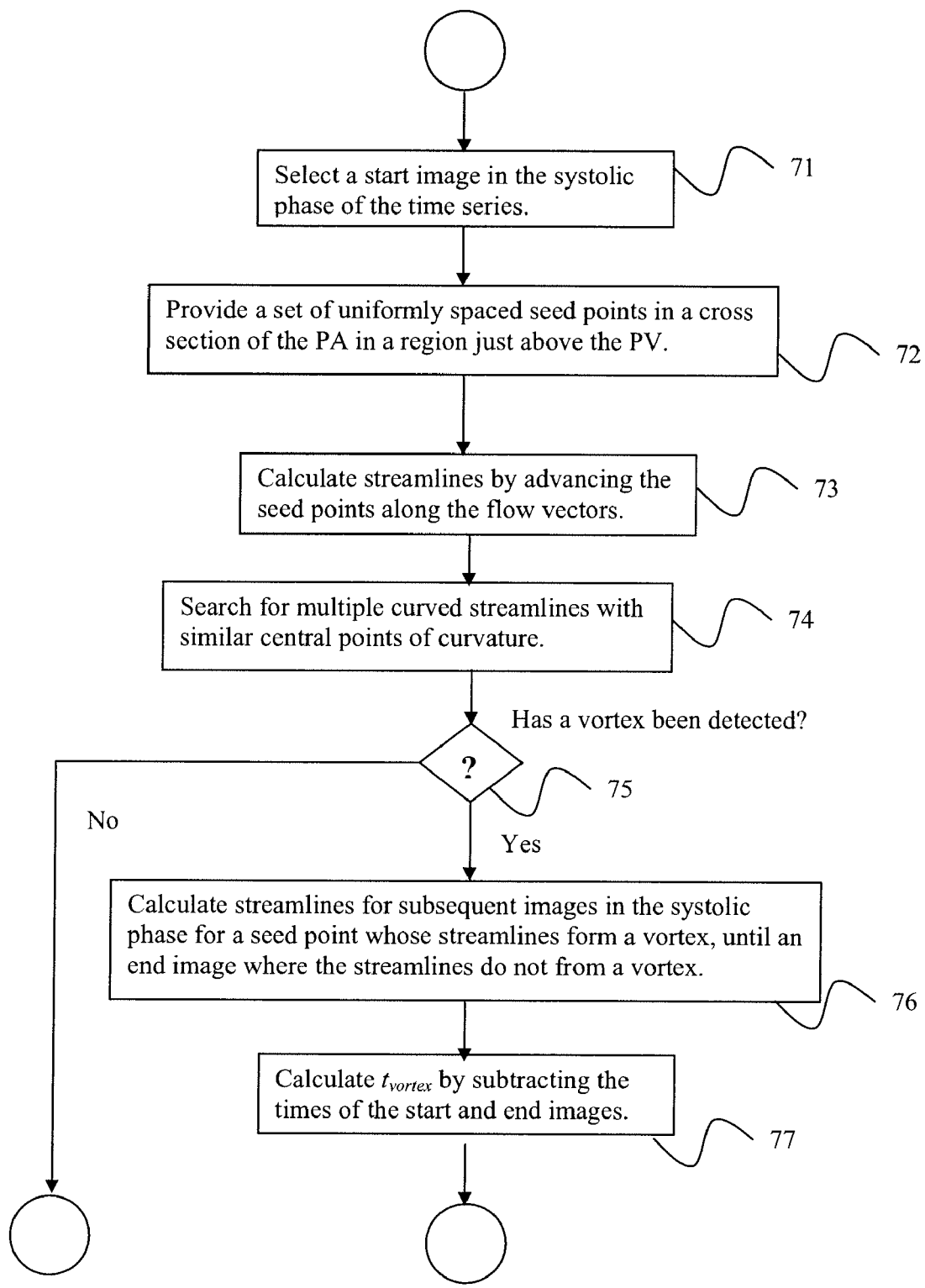
FIG. 7 is a flowchart of another method for detecting a vortex and calculating $t_{vortex}$, according to an embodiment of the invention.

An alternative method according to an embodiment of the invention for searching for a vortex is presented in FIG. 7. An alternative method begins at step 71 by selecting a start image in the systolic phase of the time series. At step 72, a set of uniformly spaced seed points is provided in a cross section of the PA in a region just above the PV. At step 73, the seed points are advanced by following the flow vectors, and this step is repeated to compute a set of streamlines. The curvature of the streamline can then be searched at step 74 for a circular pattern. Multiple lines with high degrees of curvature that share a central region of curvature is indicative of a vortex. Based on the intensity and number of such lines, a score could be computed that indicates the presence of a vortex. For example, given lines with curvature values beyond a certain threshold, a central point of curvature can be calculated. Hence, a collection of central points are determined. The location with the most central points can be deemed the vortex center. Once, at step 75, a vortex has been detected, this series of operations can be repeated at step 76 for subsequent images in the systolic phase of the time series for one or more seed points whose streamlines form parts of vortices, until a vortex is no longer detected. Once the number of central points drops below a certain value, the vortex is considered to be gone. $t_{vortex}$ is then obtained at step 77 by subtracting the times of the start and end images.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 8:
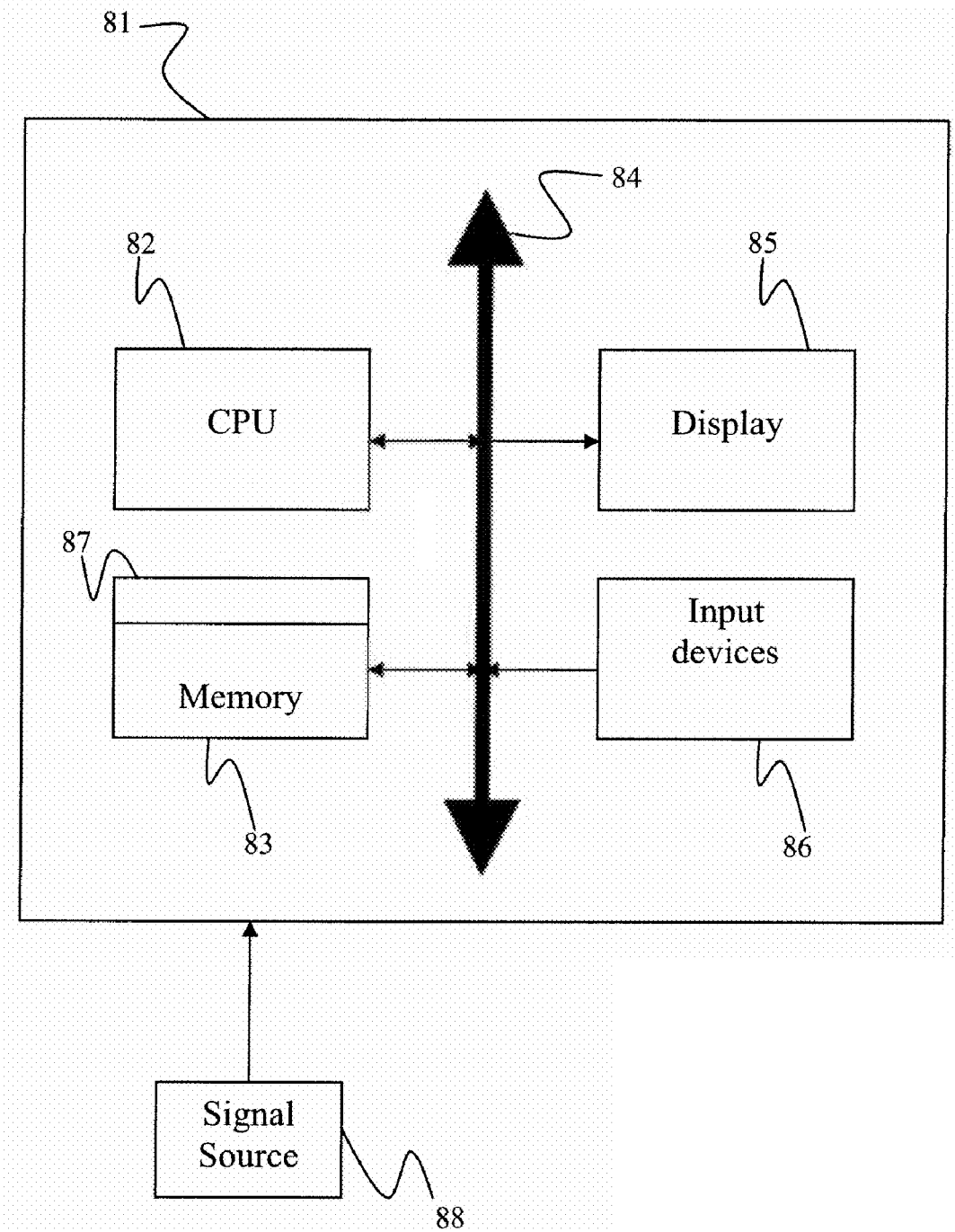
FIG. 8 is a block diagram of an exemplary computer system for implementing a method for automatic, non-invasive diagnosis of pulmonary hypertension from phase contrast magnetic resonance (MR) images, according to an embodiment of the invention.

FIG. 8 is a block diagram of an exemplary computer system for implementing a method for diagnosing pulmonary hypertension from phase contrast magnetic resonance (MR) images, according to an embodiment of the invention. Referring now to FIG. 8, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A computer-implemented method for diagnosing pulmonary hypertension from phase-contrast magnetic resonance (MR) images, the method performed by the computer comprising the steps of:
    providing a time series of one or more magnetic resonance (MR) flow images of a patient's mediastinum during one or more cardiac cycles, wherein each said flow image for a given time point comprises a plurality of 3-dimensional flow vectors associated with a 3-dimensional grid of points;
    segmenting the pulmonary artery within each image of the times series of images, and identifying the anterior wall and pulmonary valve within the segmented pulmonary artery;
    analyzing blood flow during a diastolic phase of said one or more cardiac cycles to determine a relative duration of blood flow, $t_{streamlines}$, during said diastolic phase,
    wherein analyzing blood flow to determine $t_{streamlines}$ comprises:
        selecting an image from said time series of images that is associated with a beginning of a diastolic phase;
        calculating in said selected image a spatial average of the flow magnitude in a spatial region in a cross section of the pulmonary artery;
        calculating said spatial average of said flow magnitude in each subsequent image associated with the diastolic phase until an end image is reached wherein said spatial average falls below a predetermined threshold; and
        determining $t_{streamlines}$ from differences in a time associated with said image associated with the beginning of a diastolic phase and a time associated with said end image;
    analyzing blood flow during a latter portion of a systolic phase and a subsequent diastolic phase of said one or more cardiac cycles to detect the presence and duration $t_{vortex}$ of a vortex; and
    diagnosing the presence of pulmonary hypertension from $t_{streamlines}$ and $t_{vortex}$.

2. The method of claim 1, further comprising determining said systolic and diastolic phases of each cardiac cycle from electrocardiography data acquired with said time series of said MR flow images.

3. The method of claim 1, further comprising determining said systolic and diastolic phases of each cardiac cycle by analyzing blood flow during said one or more cardiac cycles and identifying time points of maximal and minimal blood flow.

4. The method of claim 1, further comprising computing a centerline of said pulmonary artery, and using said centerline to locate said pulmonary valve.

5. The method of claim 1, wherein said spatial region in said cross section of the pulmonary artery is adjacent to the anterior wall of the pulmonary artery.

6. The method of claim 1, wherein analyzing blood flow to detect a vortex comprises:
    selecting an image from said time series of images that is associated with a systolic phase of a cardiac cycle;
    selecting a candidate vortex center point in said selected image;
    forming a first vector from said candidate vortex center point to a second point, said second point having a radius with respect to said first point;
    forming a second vector from the flow vector associated with said second point;
    calculating a sine of an angle formed by said first and second vector;
    for a set of second points forming a circle of said radius, repeating said steps of forming a second vector from a flow vector associated with said second point, and calculating a sine of an angle formed by said first and second vector, wherein said sines are summed, wherein said sum of sines is indicative of the presence of a vortex.

7. The method of claim 6, further comprising repeating said steps of forming a second vector from a flow vector associated with said second point, and calculating a sine of an angle formed by said first and second vector,
    wherein said sines are summed, for sets of points with different radii with respect to said candidate center point.

8. The method of claim 6, further comprising the steps of, for a detected vortex,
    measuring in subsequent images a sine of an angle between a first vector from a corresponding candidate vortex center point to a second point having said radius with respect to said candidate vortex center point and a second vector formed from the flow vector associated with said second point until an end image wherein said sum of sines falls below a predetermined threshold, and
    determining a time $t_{vortex}$ by subtracting a time associated with said image associated with the detection of said vortex from a time associated with said end image.

9. The method of claim 1, wherein analyzing blood flow to detect a vortex comprises
    selecting a set of seed points uniformly spaced in a cross section of said pulmonary artery above said pulmonary valve,
    computing a streamline for each seed point by repeating steps of advancing each seed point to a new point in a direction of the flow vector associated with each seed point, and resetting each seed point to each corresponding new point, for a predetermined number of iterations, and
    searching said streamlines for a circular pattern, wherein a circular pattern indicates the presence of a vortex.

10. The method of claim 9, further comprising the steps of, for a detected vortex,
calculating in subsequent images a corresponding streamline for a seed point whose streamline may be part of a vortex, until an end image is reached wherein said corresponding streamline and its neighboring streamlines no longer forms part of a vortex, and
determining a time $t_{vortex}$ from differences in a time associated with said image associated with the detection of said vortex and a time associated with said end image.

11. The method of claim 1, further comprising:
dividing a cross section of the pulmonary artery above and near to the pulmonary valve into an anterior region, a middle region, and a posterior region;
calculating a maximal flow velocity magnitude in each region for each image in at least one cardiac phase in said time series of images;
selecting a location in an image in each cardiac phase having a greatest maximal flow velocity magnitude; and
assigning a location index a value indicative of in which of said anterior region, said middle region, and said posterior region said greatest maximal flow velocity magnitude occurred, wherein said location index characterizes a blood flow velocity profile.

12. The method of claim 11, wherein if two or more regions have substantially a same greatest maximal flow velocity magnitude, assigning said location index to the average value of said corresponding regions.

13. A computer-implemented method for diagnosing pulmonary hypertension from phase-contrast magnetic resonance (MR) images, the method performed by the computer comprising the steps of:
providing a time series of one or more magnetic resonance (MR) flow images of a patient's mediastinum during one or more cardiac cycles, wherein each said flow image for a given time point comprises a plurality of 3-dimensional flow vectors associated with a 3-dimensional grid of points;
segmenting the pulmonary artery within each image of the times series of images, and identifying the anterior wall and pulmonary valve within the segmented pulmonary artery;
analyzing blood flow during a diastolic phase of said one or more cardiac cycles to determine a relative duration of blood flow, $t_{streamlines}$, during said diastolic phase;
analyzing blood flow during a latter portion of a systolic phase and a subsequent diastolic phase of said one or more cardiac cycles to detect the presence and duration $t_{vortex}$ of a vortex
wherein analyzing blood flow to detect a vortex comprises:
selecting an image from said time series of images that is associated with a systolic phase of a cardiac cycle;
selecting a candidate vortex center point in said selected image;
forming a first vector from said candidate vortex center point to a second point, said second point having a radius with respect to said first point;
forming a second vector from the flow vector associated with said second point;
calculating a sine of an angle formed by said first and second vector; and
for a set of second points forming a circle of said radius, repeating said steps of forming a second vector from a flow vector associated with said second point, and calculating a sine of an angle formed by said first and second vector, wherein said sines are summed, wherein said sum of sines is indicative of the presence of a vortex; and
diagnosing the presence of pulmonary hypertension by analyzing the location index in at least one cardiac phase in said time series of images.

14. The method of claim 13, further comprising:
dividing a cross section of the pulmonary artery above and near to the pulmonary valve into an anterior region, a middle region, and a posterior region;
calculating a maximal flow velocity magnitude in each region for each image in at least one cardiac phase in said time series of images;
selecting a location in an image in each cardiac phase having a greatest maximal flow velocity magnitude; and
assigning a location index a value indicative of in which of said anterior region, said middle region, and said posterior region said greatest maximal flow velocity magnitude occurred, wherein said location index characterizes a blood flow velocity profile.

15. The method of claim 14, further comprising selecting a location in each image in said time series of images having a greatest maximal flow velocity magnitude; and determining a location index for each phase by assigning a value indicative of in which of said anterior region, said middle region, and said posterior region said greatest maximal flow velocity magnitude occurred.

16. The method of claim 14, wherein if two or more regions have substantially a same greatest maximal flow velocity magnitude, assigning said location index to the average value of said corresponding regions.

17. The method of claim 14, further comprising using a distance transform to divide said pulmonary artery cross section into said three regions.

18. A non-transitory program storage device readable by a computer, tangibly embodying a program of instructions executable by the computer to perform the method steps for diagnosing pulmonary hypertension from phase-contrast magnetic resonance (MR) images, the method performed by the computer comprising the steps of:
providing a time series of one or more magnetic resonance (MR) flow images of a patient's mediastinum during one or more cardiac cycles, wherein each said flow image for a given time point comprises a plurality of 3-dimensional flow vectors associated with a 3-dimensional grid of points;
segmenting the pulmonary artery within each image of the times series of images, and identifying the anterior wall and pulmonary valve within the segmented pulmonary artery;
analyzing blood flow during a diastolic phase of said one or more cardiac cycles to determine a relative duration of blood flow, $t_{streamlines}$, during said diastolic phase,
wherein analyzing blood flow to determine $t_{streamlines}$ comprises:
selecting an image from said time series of images that is associated with a beginning of a diastolic phase;
calculating in said selected image a spatial average of the flow magnitude in a spatial region in a cross section of the pulmonary artery;
calculating said spatial average of said flow magnitude in each subsequent image associated with the diastolic phase until an end image is reached wherein said spatial average falls below a predetermined threshold; and determining $t_{streamlines}$ from differences in a time associated with said image associated with the beginning of a diastolic phase and a time associated with said end image;

analyzing blood flow during a latter portion of a systolic phase and a subsequent diastolic phase of said one or more cardiac cycles to detect the presence and duration $t_{vortex}$ of a vortex; and diagnosing the presence of pulmonary hypertension from $t_{streamlines}$ and $t_{vortex}$.

19. The computer readable program storage device of claim 18, the method further comprising determining said systolic and diastolic phases of each cardiac cycle from electrocardiography data acquired with said time series of said MR flow images.

20. The computer readable program storage device of claim 18, the method further comprising determining said systolic and diastolic phases of each cardiac cycle by analyzing blood flow during said one or more cardiac cycles and identifying time points of maximal and minimal blood flow.

21. The computer readable program storage device of claim 18, the method further comprising computing a centerline of said pulmonary artery, and using said centerline to locate said pulmonary valve.

22. The computer readable program storage device of claim 18, wherein said spatial region in said cross section of the pulmonary artery is adjacent to the anterior wall of the pulmonary artery.

23. The computer readable program storage device of claim 18, wherein analyzing blood flow to detect a vortex comprises:
    selecting an image from said time series of images that is associated with a systolic phase of a cardiac cycle;
    selecting a candidate vortex center point in said selected image;
    forming a first vector from said candidate vortex center point to a second point, said second point having a radius with respect to said first point;
    forming a second vector from the flow vector associated with said second point;
    calculating a sine of an angle formed by said first and second vector;
    for a set of second points forming a circle of said radius, repeating said steps of forming a second vector from a flow vector associated with said second point, and calculating a sine of an angle formed by said first and second vector, wherein said sines are summed, wherein said sum of sines is indicative of the presence of a vortex.

24. The computer readable program storage device of claim 23, the method further comprising repeating said steps of forming a second vector from a flow vector associated with said second point, and calculating a sine of an angle formed by said first and second vector, wherein said sines are summed, for sets of points with different radii with respect to said candidate center point.

25. The computer readable program storage device of claim 23, the method further comprising the steps of, for a detected vortex, measuring in subsequent images a sine of an angle between a first vector from a corresponding candidate vortex center point to a second point having said radius with respect to said candidate vortex center point and a second vector formed from the flow vector associated with said second point until an end image wherein said sum of sines falls below a predetermined threshold, and determining a time $t_{vortex}$ by subtracting a time associated with said image associated with the detection of said vortex from a time associated with said end image.

26. The computer readable program storage device of claim 18, wherein analyzing blood flow to detect a vortex comprises selecting a set of seed points uniformly spaced in a cross section of said pulmonary artery above said pulmonary valve, computing a streamline for each seed point by repeating steps of advancing each seed point to a new point in a direction of the flow vector associated with each seed point, and resetting each seed point to each corresponding new point, for a predetermined number of iterations, and searching said streamlines for a circular pattern, wherein a circular pattern indicates the presence of a vortex.

27. The computer readable program storage device of claim 26, the method further comprising the steps of, for a detected vortex, calculating in subsequent images a corresponding streamline for a seed point whose streamline may be part of a vortex, until an end image is reached wherein said corresponding streamline and its neighboring streamlines no longer forms part of a vortex, and determining a time $t_{vortex}$ from differences in a time associated with said image associated with the detection of said vortex and a time associated with said end image.

28. The computer readable program storage device of claim 18, the method further comprising:
    dividing a cross section of the pulmonary artery above and near to the pulmonary valve into an anterior region, a middle region, and a posterior region;
    calculating a maximal flow velocity magnitude in each region for each image in at least one cardiac phase in said time series of images;
    selecting a location in an image in each cardiac phase having a greatest maximal flow velocity magnitude; and
    assigning a location index a value indicative of in which of said anterior region, said middle region, and said posterior region said greatest maximal flow velocity magnitude occurred, wherein said location index characterizes a blood flow velocity profile.

29. The computer readable program storage device of claim 28, wherein if two or more regions have substantially a same greatest maximal flow velocity magnitude, assigning said location index to the average value of said corresponding regions.

30. The method of claim 14, further comprising selecting a location in an image in each phase of a cardiac cycle having a greatest maximal flow velocity magnitude; and determining a location index for each phase by assigning a value indicative of in which of said anterior region, said middle region, and said posterior region said greatest maximal flow velocity magnitude occurred.

31. The method of claim 13, further comprising repeating said steps of forming a second vector from a flow vector associated with said second point, and calculating a sine of an angle formed by said first and second vector,
    wherein said sines are summed, for sets of points with different radii with respect to said candidate center point.

32. The method of claim 31, further comprising the steps of, for a detected vortex,
    measuring in subsequent images a sine of an angle between a first vector from a corresponding candidate vortex center point to a second point having said radius with respect to said candidate vortex center point and a second vector formed from the flow vector associated with said second point until an end image wherein said sum of sines falls below a predetermined threshold, and
    determining a time $t_{vortex}$ by subtracting a time associated with said image associated with the detection of said vortex from a time associated with said end image.

* * * * *